US00RE35076E

United States Patent [19]

Nakamura

[11] E Patent Number: Re. 35,076

[45] Reissued Date of Patent: Oct. 31, 1995

[54] ENDOSCOPE APPARATUS FOR DISPLAYING IMAGES BELOW THE MUCOUS MEMBRANCE

[75] Inventor: Kazunari Nakamura, Hachioji, Japan

[73] Assignee: Olympus Optical Co., Ltd., Tokyo, Japan

[21] Appl. No.: 780,642

[22] Filed: Oct. 18, 1991

Related U.S. Patent Documents

Reissue of:

[64] Patent No.: 4,945,409
Issued: Jul. 31, 1990
Appl. No.: 247,194
Filed: Sep. 21, 1988

[51] Int. Cl.[6] ..... H04N 7/18; H04N 5/335; A61G 1/06

[52] U.S. Cl. ..... 348/70; 348/162

[58] Field of Search ..... 358/98, 110; 128/6, 128/4; 348/70, 162

[56] References Cited

U.S. PATENT DOCUMENTS 4,562,831 1/1986 Murakashi et al. ..... 358/98
4,656,508 4/1987 Yokota ..... 338/98

FOREIGN PATENT DOCUMENTS 56-3033 1/1981 Japan .

*Primary Examiner*—John K. Peng
*Assistant Examiner*—Edward Lefkowitz
*Attorney, Agent, or Firm*—Armstrong, Westerman, Hattori, McLeland & Naughton

[57] ABSTRACT

An endoscope whereby the vein image below the mucous membrane within a body cavity or the like can be observed has an insertable part to be inserted into the body cavity and is provided with an illuminating window and observing window in the tip part of the insertable part. A light guide transmitting an illuminating light emitted from a light source is inserted through the insertable part. The illuminating light transmitted through the light guide is emitted from the illuminating window to illuminate an object to be observed. The reflected light from the object forms an image in an imaging apparatus through the observing window and the formed object is converted to an electric signal. A light separating filter separating the light entering the imaging apparatus into a plurality of wavelength bands is provided between the light source part and imaging apparatus. The output signal of the imaging apparatus is processed by a video signal processing circuit and is input into an operating circuit. This operating circuit operates the video signals relating to at least two wavelength bands which are output signals of the video signal processing circuit and outputs the result. The output of the operating circuit is delivered to a picture image displaying monitor.

32 Claims, 7 Drawing Sheets

MOTOR DRIVER
POWER SUPPLY
MOTOR
SYNCHRO. C. C.
CCD DRIVER
CHANGING C. C.
SUBTRACTION C. C.
D/A
FRAME MEMORY
FRAME MEMORY
FRAME MEMORY
FRAME MEMORY
FRAME MEMORY
A/D
VIDEO PROCESS. C. C.
LEVEL-SENSE C. C.
PRE-AMPLIFIER
1
2
3
4
5
6
7a
7b
8
9
10
11
12
13
14
15
16
18
19
20
21
22
23a
23b
23c
23d
23e
24
25
26
27

30
31
MOVEMENT CONTR. C.C.
34
32
MOTOR
14
MOTOR DRIVER
13
POWER SUPPLY
12
11
15
35
4
3
6
5
CCD DRIVER
18
SYNCHRO. C. C.
25
CHANGING C. C.
33
PRE - AMPLIFIER
19
LEVEL SENSE C. C.
20
37
VIDEO PROCESS. C. C.
21
A/D
22
38b
FRAME MEMORY
FRAME MEMORY
FRAME MEMORY
38d
38c
SUBTRACTION C. C.
24
D/A
27
8

ENDOSCOPE APPARATUS FOR DISPLAYING IMAGES BELOW THE MUCOUS MEMBRANCE

Matter enclosed in heavy brackets [ ] appears in the original patent but forms no part of this reissue specification; matter printed in italics indicates the additions made by reissue.

BACKGOUND OF THE INVENTION:

This invention relates to an endoscope apparatus whereby the vein image or the like below the mucous membrane within a body cavity or the like can be observed.

Recently, various electronic endoscopes (also called electronic scopes) wherein a solid state imaging device such as a charge coupled device is used as an imaging means, have been suggested.

Such an electronic endoscope has advantages because the resolution is higher than in a fiber scope, it is easy to record and reproduce picture images and picture image processes such as enlargement and comparison of two picture images are easy.

Now, when distinguishing the affected part and normal part from each other by observing the observed part with the above mentioned electronic endoscope, it will be necessary to sense (recognize) a delicate tone difference.

However, when the variation of the tone of the observed part is delicate, in order to detect this delicate difference, a lot of knowledge and experience will be required and further a long time will be required until it is sensed. Even if attention is concentrated during the sensing, it has been difficult to always make a proper determination.

In order to cope with such circumstances, for example, in the publication of a Japanese patent application of a Japanese patent application laid open No. 3033/1981, there is disclosed a technique wherein, by noting that, in a range other than the visible range as, for example, an infrared wavelength range, some variation of the tone will be large, a spectral light having at least one infrared wavelength range is led in time series to illuminate an object to be observed. The reflected light from the observed object is made to form an image on a solid state imaging device. The image is converted to an electric signal and the electric signal is processed in response to the wavelength range so that a picture image in the wavelength range may be displayed by a specific color signal.

Generally, in an electronic endoscope, a solid state imaging device is photosensitive even to an infrared wavelength range and therefore the image information of the infrared wavelength range can be detected. However, when coloring the image, the image information of the infrared wavelength range will be in the way of balancing the colors. Therefore, in order to elevate the fidelity of the colors, usually, the illuminating light of the infrared wavelength range is prevented by an infrared ray cutting filter or the like from being radiated to the observed object or will be prevented by a provided filter from reaching the light receiving surface of the solid state imaging device even if it is radiated.

According to this prior art example, by using the feature that the light in the infrared range is higher in the penetration degree into a living body or the like than in the visible light range, the observation and recording of an image below the mucous membrane such as the part observed in the infrared range which have been difficult with the observation of the observed part in the visible light range are made possible.

This enables, for example, the vein running state below the mucous membrane of an organ to be accurately observed and becomes a help in determining the affected part or the like.

However, in the above mentioned prior art example, for example, an image of a thick vein near the mucous membrane surface can be sensed in the observed part but, as the illuminating light is reflected on the mucous membrane surface in this observed part, the resolution of the image below the mucous membrane will not rise and it has been difficult to sense the information over the details below the mucous membrane.

OBJECT AND SUMMARY OF THE INVENTION:

An object of the present invention is to provide an endoscope whereby the running state of minute veins below the mucous membrane and an affect part can be observed at a high resolution by removing the reflected light on the mucous membrane surface in the observed part.

The above mentioned object is attained by providing an endoscope including a light separating device and operating device. The endoscope has a light separating device separating an illuminating light into a plurality of wavelength bands between a light source part emitting the illuminating light and an imaging device electrically converting an object image. The output signal of the imaging device will be processed to be a video signal by a video signal processing device and will be input into an operating means. The operating device will operate at least two video signals among the video signals output from the video signal processing device and corresponding to different wavelength bands to take out and output the video information of the other included in the video information corresponding to one video signal. The output of the operating device will be delivered to a monitor displaying the picture image.

BRIEF DESCRIPTION OF THE DRAWING:

FIG. 1 is an explanatory view showing an entire endoscope imaging apparatus.

FIG. 2 is an elevation of a rotary filter provided with five wavelength range transmitting filters.

FIG. 3 is an explanatory diagram showing the transmitting characteristics of the five wavelength range transmitting filters in the rotary filter.

FIG. 4 is an explanatory diagram showing the characteristics of absorbing hemoglobin in a blood by illuminating light of respective wavelengths.

FIG. 5 is an explanatory diagram showing the formation of an entire endoscope imaging apparatus.

FIG. 6 is an elevation of a rotary filter provided with three wavelength range transmitting filters.

FIG. 7 is an explanatory diagram showing the transmitting characteristics of the three wavelength range transmitting filters in the rotary filter.

FIG. 8 is an explanatory diagram showing the formation of an entire endoscope imaging apparatus.

FIG. 9 is an explanatory view showing an array of color filters placed in front of a solid state imaging device.

FIG. 10 is an explanatory diagram showing the spectral output characteristics of the solid state imaging device.

DETAILED DESCRIPTION OF PREFERRED EMBODIMENTS:

FIGS. 1 to 4 show the first embodiment of the present invention.

In this embodiment, the present invention is applied to an electronic endoscope imaging apparatus in which a frame sequential system is adopted.

Figure 1:
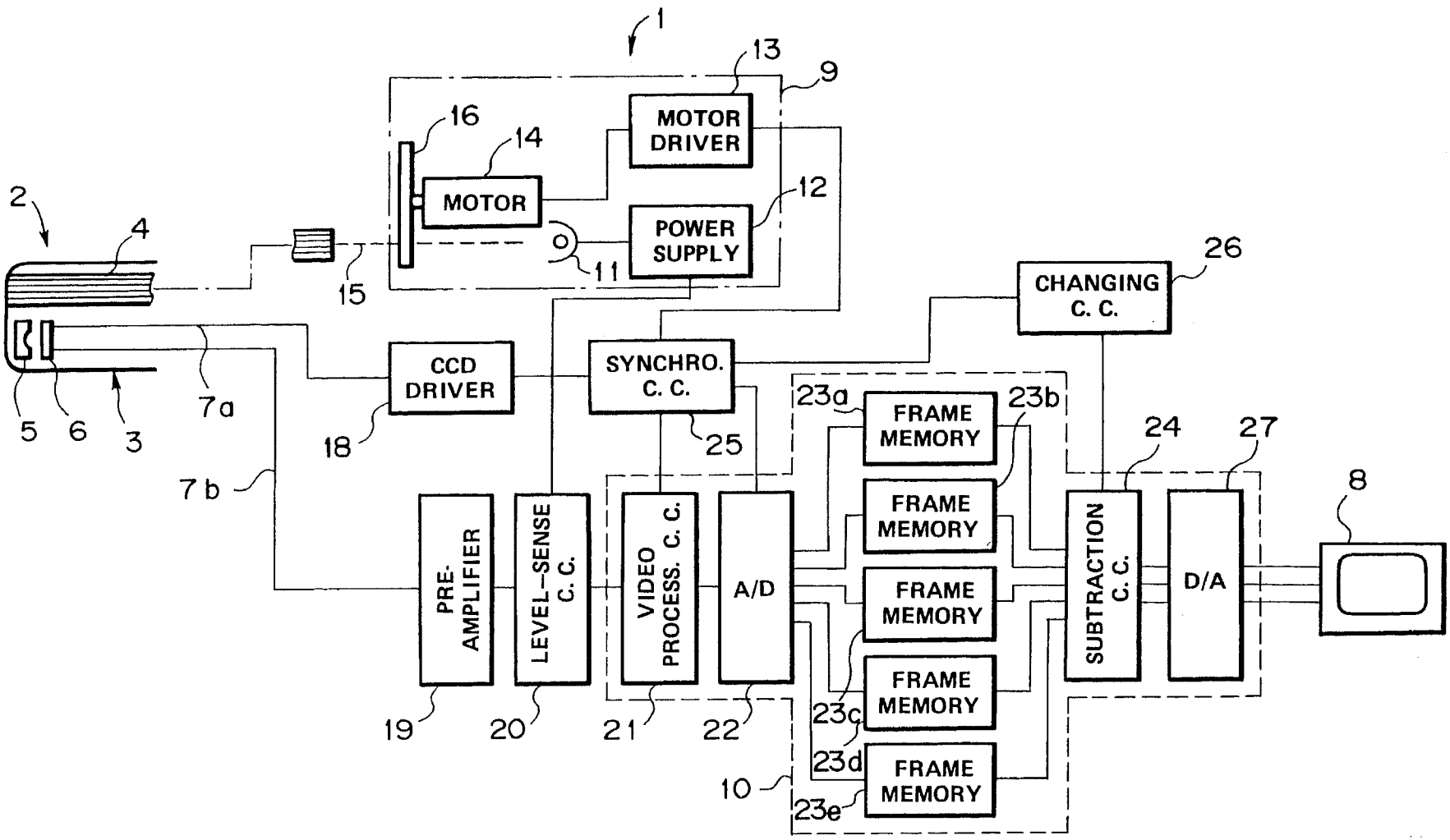
FIGS. 1 to 4 relate to the first embodiment of the present invention.

As shown in FIG. 1, an endoscope 2 fitted to an endoscope imaging apparatus 1 comprises an elongated flexible insertable part 3 and an operating part (not illustrated) provided in the rear of the insertable part 3. A light guide 4 leading an illuminating light is inserted through the insertable part 3 and operating part (not illustrated) of the above mentioned endoscope 2. An observing optical system 5 consisting of an objective lens or the like receiving an observed image light obtained when an illuminating light is radiated to an observed part is arranged in the tip part of the above mentioned insertable part 3. A solid state imaging device 6 consisting of a charge coupled device (CCD) or the like is arranged in the position where the observed image light is made to form an image by this observing optical system. This solid state imaging device is connected into the later described endoscope imaging apparatus 1 through signal lines 7a and 7b.

Further, the endoscope imaging apparatus 1 is connected to a television monitor 8 so that the observed part image may be output as a video image.

The endoscope imaging apparatus 1 is formed of a light source part 9 wherein an illuminating light adapted to a frame sequential system is obtained, a control part 10 processing the video signal and detecting the signal difference and others described later.

The above mentioned light source part 9 is provided with a lamp 11 emitting an illuminating light having a wavelength in an ultraviolet light range to a visible light range and further to an infrared range and a lamp power source circuit 12 feeding an electric power to this lamp 11 and having the exposure adjusted by a later described level sensing circuit 20.

In such a case, for example, a xenon lamp, halogen lamp or strobolamp will be used for the lamp 11.

The above mentioned light source part 9 has a motor driving circuit 13 controlled by a synchronous signal generating circuit 25, a motor 14 connected to this motor driving circuit 13 and a rotary filter 16 provided on the rotary shaft of this motor 14 and interposed in an optical axis 15 connecting the above mentioned lamp 11 with the above mentioned light guide 4 on the entrance end surface.

Figure 2:
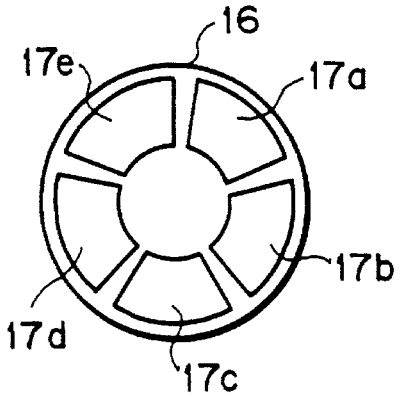

As shown in FIG. 2, the above mentioned rotary filter 16 has a wavelength range transmitting filter 17a transmitting a wavelength range of red (R), a wavelength range transmitting filter 17b transmitting a wavelength range of green (G), a wavelength range transmitting filter 17c transmitting a wavelength range of blue (B), a wavelength range transmitting fiber 17a transmitting a wavelength range of infrared (IR) and a wavelength range transmitting filter 17e transmitting a wavelength range of ultraviolet (UV) arranged in the peripheral direction.

Now, the CCD driving circuit 18 controlled by the above mentioned synchronous signal generating circuit 25 is connected through a signal line 7a with the solid state imaging device 6 arranged on the tip side of the above mentioned insertable part. The above mentioned solid state imaging device 6 is connected through a signal line 7b to a pre-amplifying circuit 19 amplifying the electric signal photoelectrically converted from the observed image light by this solid state imaging device.

The above mentioned pre-amplifying circuit 19 is connected to a level sensing circuit 20 which determines the strength of the photoelectric signal including the picture image information amplified by the above mentioned pre-amplifying circuit 19. This level sensing circuit 20 is connected to the above mentioned lamp power source circuit 20 to control it.

Further, the above mentioned level sensing circuit 20 is to be connected to the control part 10 processing a video image and sensing a signal difference.

The above mentioned control part 10 is provided with a video signal processing circuit 21 controlled by the synchronous signal generating circuit 25, connected to the above mentioned level sensing circuit 20 and processing a video signal and an A/D converting circuit 22 connected to this video signal processing circuit 21, controlled the same by the synchronous signal generating circuit 25 and converting an analogue signal to a digital signal. Following this A/D converting circuit 22, the above mentioned [contact circuit] *control part* 10 is provided with a frame memory 23a storing the video signal of the observed part obtained by radiating the illuminating light having passed through the red (R) wavelength transmitting filter 17a, a frame memory 23b storing the video signal of the same obtained by the illuminating light having passed through the green (G) wavelength range transmitting filter 17b, a frame memory 23c storing the video signal obtained by the illuminating light having passed through the blue (B.) wavelength range transmitting filter 17c, a frame memory 23d storing the video signal obtained by the illuminating light having passed through the infrared (IR) wavelength range transmitting filter 17dand a frame memory 23e storing the video signal obtained by the illuminating light having passed through the ultraviolet (UV) wavelength range transmitting filter 17e.

The above mentioned frame memories 23a, 23b, 23c, 23d and 23e are connected to a subtracting circuit 24 which is controlled by a changing circuit 26 designating any plurality of video signals of these frame memories 23a, 23b, 23c, 23d and 23e and controlled by the synchronous signal generating circuit 25 and detects the signal difference of any plurality of video signals.

Further, the video signal processed by the above mentioned subtracting circuit 24 is converted from the digital signal to an analogue signal by a D/A converting circuit 27 and is output in the television monitor 8.

Now, the synchronous signal generating circuit 25 generates a reference signal synchronizing the timing of respective active circuits and controls the entire endoscope apparatus 1.

The operation of the thus formed first embodiment shall be explained in the following.

Figure 3:
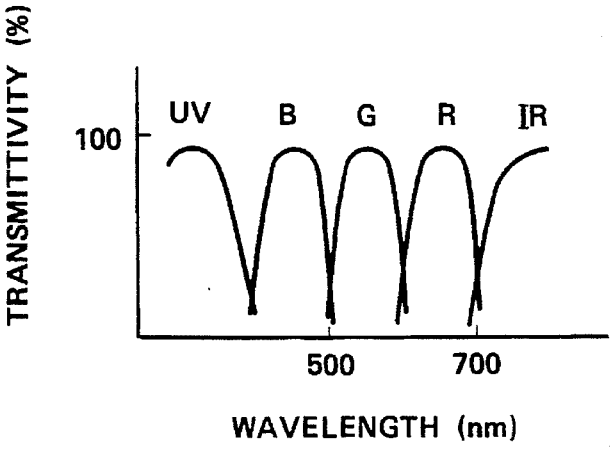

The illuminating light emitted from the lamp 11 lighted with an electric power fed from the lamp power source circuit 12 will enter the rotary filter 16 along the optical axis 15. This rotary filter 16 will be rotated by the motor 14 rotated and controlled by the motor driving circuit 13 into which the reference signal output from the synchronous signal generating circuit 25 is input and the wavelength range transmitting filters 17a, 17b, 17c, 17d and 17e provided in the peripheral direction of the above mentioned rotary filter 16 will be interposed in the optical axis 15 in turn. Depending on the respective transmitting filters 17a, 17b, 17c, 17d and 17e, the illuminating light will be separated into the respective wavelength ranges of red (R), green (G), blud (B), infrared (IR) and ultraviolet (UV) as shown in FIG. 3. At this time, the illuminating light will be separated in time series into the respective wavelength ranges in response to the rotating speed of the rotary filter 16 and will enter the light guide 4 on the entrance end surface. The illuminating light entering as separated in time series into the respective wavelength ranges will be led by the light guide 4 and will be emitted from the exit end surface of this light guide 4 to illuminate a part to be observed such as the body cavity interior of a living body (not illustrated).

At this time, the respective illuminating light separated into the respective wavelength ranges, that is, of red (R), green (G), blue (B), infrared (IR) and ultraviolet (UV) will be different when reflected from the surface layer part of the observed part and particularly, the longer the wavelength, the deeper the illuminating light penetrates into the observed part. (This degree shall be called a penetrating degree hereinafter.)

Therefore, when the illuminating light separated in time series into the respective wavelength ranges, that is, of red (R), green (G), blue (B), infrared (IR) and ultraviolet (UV) are radiated to the observed part, observed image light corresponding to the respective penetrating degree will be obtained.

The observed image light corresponding in time series to the respective penetrating degrees will be made to form images in turn on the solid state imaging device 6 by the observing optical system 5. This solid state imaging device 6 will be driven and controlled by the CCD driving circuit 18 controlled by the reference signal of the synchronous signal generating circuit 25, will photoelectrically convert in turn the observed image light corresponding to the respective penetrating degrees and will output electric signals having picture image information corresponding to the respective penetrating degrees.

The above described electric signals will be amplified by the pre-amplifying circuit 19.

The electric signals corresponding to the respective penetrating degrees through this pre-amplifying circuit 19 will have the exposures sensed by the level sensing circuit 20 and the electric power fed by the above mentioned lamp power source circuit 12 will be adjusted to adjust the exposure.

Then, the electric signals including the picture image information corresponding to the penetrating degrees by the illuminating light of the red (R), green (G), blue (B), infrared (IR) and ultraviolet (UV) wavelength ranges will be processed to be video signals by correcting $\gamma$, tone and respective wavelength range gains in the video signal processing circuit 21 controlled by the reference signal of the synchronous signal generating circuit 25, will be further converted to digital signals by the A/D converting circuit 22 controlled by the synchronous signal generating circuit 25 and will be output in turn to the frame memories 23a, 23b, 23c, 23d and 23e. That is to say, the digital signal including the picture image information corresponding to the penetrating degree by the illuminating light of the red (R) wavelength range will be stored in the frame memory 23a. In the same manner, the digital signal including the picture image information of green (G) will be stored in the frame memory 23b, the digital signal including the picture image information of blue (B) will be stored in the frame memory 23c, the digital signal including the picture image information of infrared (IR) will be stored in the frame memory 23d and the digital signal including the picture image information of ultraviolet (UV) will be stored in the frame memory 23e in turn.

Figure 4:
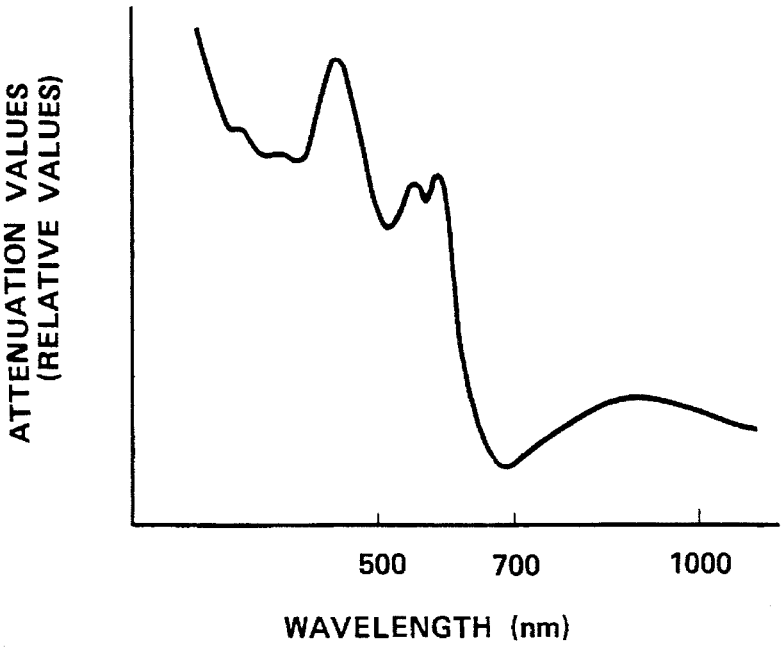

Now, the tone of the observed part on the inside wall of an organ or the like within the living body or, for example, the tone of the stomach mucous membrane or the like as an observed part greatly depends on the hemoglobin existing in the blood. As shown in FIG. 4, the illuminating light absorbing characteristics in the respective wavelengths of this hemoglobin are greatly different depending on the wavelength ranges. In FIG. 4, the wavelength ranges from the ultraviolet (UV) to blue (B), when made illuminating light, will be large in the amount of the illuminating light absorbed by hemoglobin, that is, in the amount of attenuation of the illuminating light and therefore only the information of the surface state of the mucous membrane will be obtained. The wavelength ranges from red (R) to infrared (IR) are so small in the amount of attenuation of the illuminating light in hemoglobin that not only information about the mucous membrane surface but also information about the penetrating range of the disease or the running state of the vein image below the mucous membrane will be obtained.

Therefore, when the digital signals including the picture image information corresponding to the penetrating degrees by the illuminating light of the respective wavelength ranges are stored in turn in the frame memories 23a, 23b, 23c, 23d and 23e, the signal difference between the frame memories 23c and 23e storing the picture image signals of the wavelength ranges from ultraviolet (UV) to blue (B) including the information about the mucous membrane surface and the frame memories 23a and 23d storing the picture image signals of the wavelength ranges from red (R) to infrared (IR) including the information about the mucous membrane surface and the information below the mucous membrane will be detected, that is, subtracted by the subtracting circuit 24 by setting the changing circuit 26 controlled by the reference signal of the synchronous signal generating circuit 25.

In this subtracting circuit 24, the picture image signals including the information of the mucous membrane surface, that is, the picture image signals stored in the frame memories 23c and 23e are subtracted from the picture image signals including the information of the mucous membrane surface and below the mucous membrane, [that it,] *that is* the picture image signals stored in the frame memories 23a and 23d.

Therefore, a digital signal having the picture image information of the penetrating range of the disease or the running state of the vein image below the mucous membrane will be obtained, will be converted to an analogue signal by the D/A converter 27 and will be output as a video image to the television monitor 8.

Here, if the information of the video signals of the respective wavelength ranges of red (R), green (G), blue (B), infrared (IR) and ultraviolet (UV) are stored respectively in the frame memories 23a, 23b, 23c, 23d and 23e, by setting the above mentioned changing circuit 26, picture image information in any plurality of wavelength ranges will be able to be subtracted.

Thus, according to this embodiment, by the difference between the penetrating degrees of the illuminating light in the respective wavelength ranges, for example, the penetrating range of the disease and the running state of the vein image below the mucous membrane of the inside wall of an organ or the like of the living body will not be influenced by the reflection of the illuminating light on the mucous membrane surface and the part to be observed can be observed at a high resolution.

By taking out the illuminating light of the wavelength range of ultraviolet (UV) by subtraction, a picture image, from which the minute information of the surface in the observed part is obtained, can be obtained.

Also, the picture images in the wavelength ranges of infrared (R) and ultraviolet (UV) can be displayed not only in monochrome but also in quasi colors.

Figure 5:
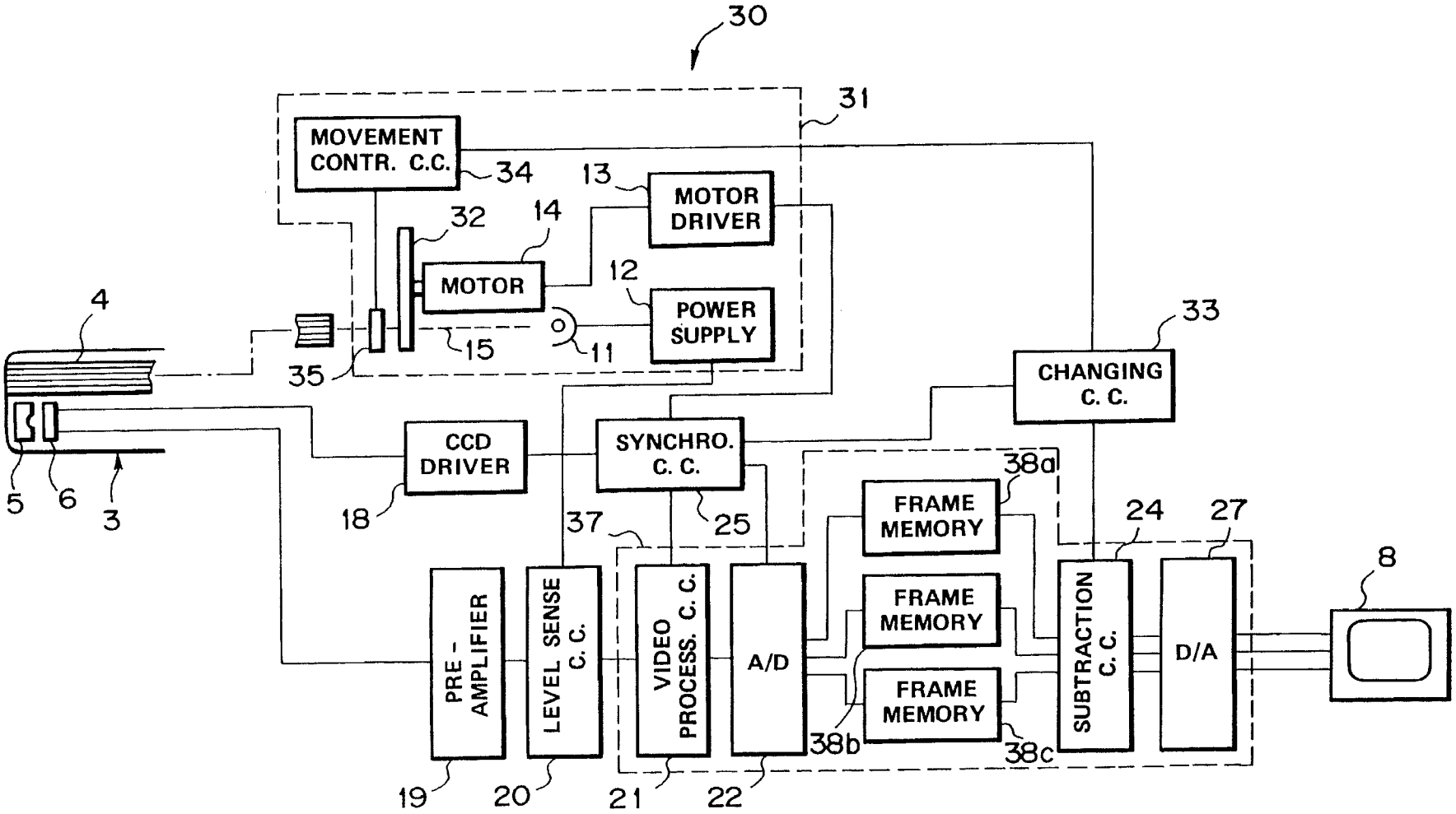
FIGS. 5 to 7 relate to the second embodiment of the present invention.
Figure 6:
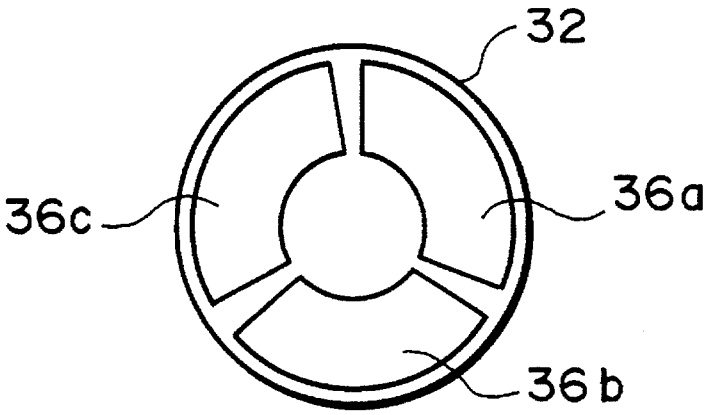
Figure 7:
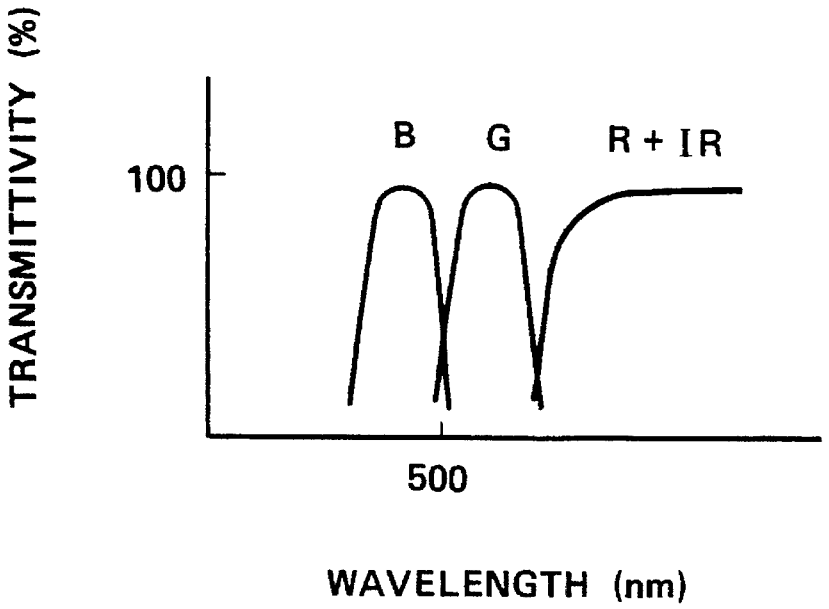

FIGS. 5 to 7 show the second embodiment of the present invention.

The same as in the first embodiment, this embodiment is applied to an electronic endoscope imaging apparatus in which a frame sequential system is adopted.

Therefore, the formation which is different from the first embodiment of the endoscope imaging apparatus 30 shall be described.

A light source part 31 provided within the endoscope imaging apparatus 30 is provided with a lamp 11 emitting illuminating light in the ultraviolet range, visible light range and infrared range and a lamp power source circuit 12 feeding an electric power to this lamp 11 and having the exposure adjusted by a level sensing circuit 20.

The above mentioned light source part 31 has a motor driving circuit 13 controlled by a synchronous signal generating circuit 25, a motor 14 connected to this motor driving circuit 13, a rotary filter 32 provided on the rotary shaft of this motor 14 and interposed in the optical axis 15 connecting the lamp 11 with a light guide 4 on the entrance end surface, a filter removably interposing means 34 controlled by the synchronous signal generating circuit 25 and set by a changing circuit 33 and an infrared cutting filter 35 removable interposed in the optical axis 15 by this filter removably interposing means 34 and cutting the illuminating light in the infrared wavelength range.

As shown in FIG. 6, in the above mentioned rotary filter 32, a wavelength range transmitting filter 36a having a transmitting characteristic in the wavelength range of green (G), a wavelength range transmitting filter 36b having a transmitting characteristic in the wavelength range of blue (B) and a wavelength ranges transmitting filter [36] *36c* having a transmitting characteristic in the wavelength ranges of red and infrared (R+IR) are arranged in the peripheral direction.

A controlling part 37 processing video signal and sensing a signal difference or the like is provided with a frame memory 38a storing the video signal of the observed part obtained by radiating the illuminating light having passed through the green (G) wavelength range transmitting filter 36a in the above mention rotary filter 32, a frame memory 38b storing the video signal obtained by the illuminating light having passed through the blue (B) wavelength range transmitting filter 36b in the same manner and a frame memory 38c storing the video signal obtained by the illuminating light having passed through the red and infrared (R+IR) wave length range transmitting filter 36c.

The other formations in the second embodiment are the same as in the first embodiment.

The operation of the thus formed second embodiment shall be explained in the following.

First of all, when the filter removably interposing means 34 is operated by the changing circuit 33, the infrared cutting filter 35 will be removed from the optical axis 15 shall be explained.

The illuminating light emitted from the lamp 11 will enter the rotary filter 32 along the optical axis 15. This rotary filter 32 will be rotated and driven by the motor 14 and the wavelength range transmitting filters 36a, 36b and 36c provided in the peripheral direction of the rotary filter 32 will be interposed in the optical axis 15 in turn. By the respective transmitting characteristics of these wavelength range transmitting filters 36a, 36b and 36c, the above mentioned illuminating light will be separated into illuminating light respectively of green (G), blue(B) and red and infrared (R+IR). At this time, the illuminating light will be separated into the respective wavelength ranges in time series in response to the rotating speed of the rotary filter 32, will enter the light guide 4 on the entrance end surface, will be led by the light guide 4, will be emitted from the light guide on the exit end surface and will illuminate such observed part as the body cavity interior of a living body.

At this time, the penetrating degrees into the mucous membrane surface layer in the observed part will be different in response to the respective illuminating light of the respective wavelength ranges, that is, of green (G), blue (B) and red and infrared (R+IR). That is to say, the illuminating light of the long infrared (IR) wavelength range will be larger in the penetrating degree than the illuminating light of the blue (B) wavelength range.

Therefore, observed image light different in the penetrating degree in response to green (G), blue (B) and red and infrared (R+IR) will be obtained in time series.

The observed image light will be made to form images on the solid state imaging device 6 by the observing optical system 5 and will be output as electric signals having picture image information of the observed image light in response to the respective penetrating degrees by this solid state imaging device.

The above mentioned respective electric signals will be amplified by the pre-amplifying circuit 19, will be processed to be video signals by having the $\gamma$, tone and respective wavelength range gains corrected by the video signal processing circuit 21 through the level sensing circuit 20 adjusting the exposure by transmitting the signals to the lamp power source circuit 12 and will be further converted to digital signals by the A/D converting circuit 22.

The digital signal including the picture image information corresponding to the penetrating degree by the illuminating light of the green (G) wavelength range will be stored in the frame memory 38a, in the same manner, the digital signal including the picture image information of green (G) will be stored in the memory 38b and the digital signal including the picture image information of red and infrared (R+IR) will be stored in the frame memory 38c in turn.

Now, as in the first embodiment, the tone of an observed part as, for example, the stomach mucous membrane, depends mostly on the hemoglobin in the blood which has different absorbing characteristics of the illuminating light in respective wavelengths as are shown in FIG. 4.

Therefore, when the digital signals, including the picture image information corresponding to the penetrating degrees by the illuminating light of the respective wavelength ranges, are stored in turn in the frame memories 38a, 38b and 38c, the subtraction of the frame memory 38b storing the picture image signal of the blue (B) wavelength range including mostly the information about the mucous membrane surface and the frame memory 38c storing the picture image signals of the red and infrared (R+IR) wavelength ranges including the information about the mucous membrane surface and below the mucous membrane will be made by the subtracting circuit 24 by setting the changing circuit 33 controlled by the reference signal of the synchronous signal generating circuit [25"] *25*.

Thus, the digital signal having the picture image information of the information below the mucous membrane, that is, of the penetrating range of the disease or the running state of the vein image is obtained.

Further, the above mentioned digital signals are converted to analogue signals by the D/A converter 27 and are output as video images to the television monitor 8.

When the filter removably interposing means 34 is operated by the changing circuit 33 and the infrared cutting filter 35 is interposed in the optical axis 15 shall be explained.

The illuminating light emitted from the lamp 11 will be separated into illuminating light of respective green (G), blue (B) and red and infrared (R+IR) wavelength ranges by the respective characteristics of the wavelength range transmitting filters 36a, 36b and 36c provided in the rotary filter 32.

Further, by the infrared cutting filter 35 interposed in the optical axis 15 forward of the above mentioned rotary filter 32, the illuminating light separated into the above mentioned respective wavelength ranges will become illuminating light of the green (G), blue (B) and red (R) wavelength ranges.

The observed image light obtained by radiating the illuminating light to the observed part will become respective green (G), blue (B) and red (R) wavelength ranges.

Therefore, in this embodiment when the filter [36] *35* is interposed, in addition to the operation and effect in the first embodiment, as the number of the wavelength range transmitting filters 36a, 36b and 36c is smaller than of the wavelength range transmitting filters 17a, 17b, 17c, 17d and 17e in the first embodiment, the relative aperture rate of the transmitting filters 36a, 36b and 36c will be high. Therefore, the observed part can be illuminated at a high illuminating degree and information about the deeper part of the mucous membrane layer can be obtained when the filter is interposed.

Figure 8:
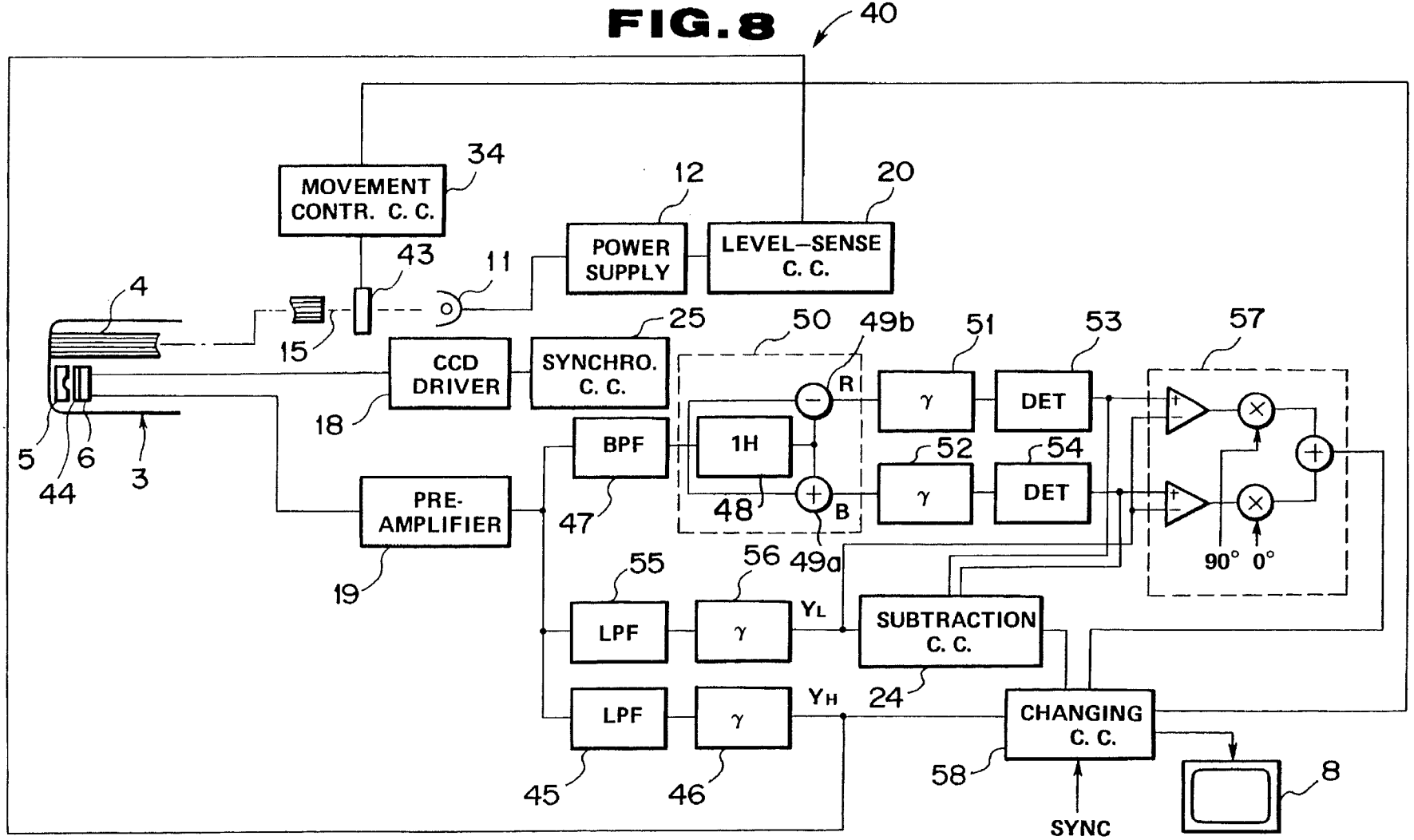
FIGS. 8 to 10 relate to the third embodiment of the present invention.
Figure 9:
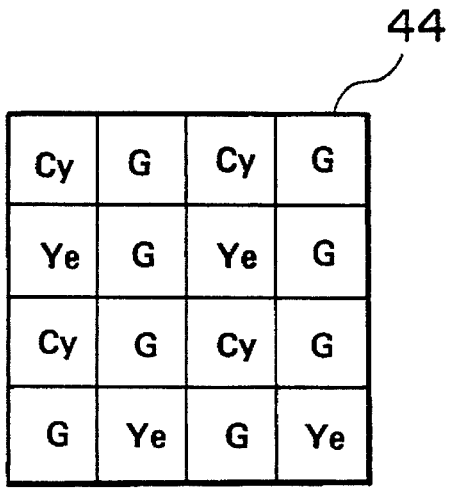
Figure 10:
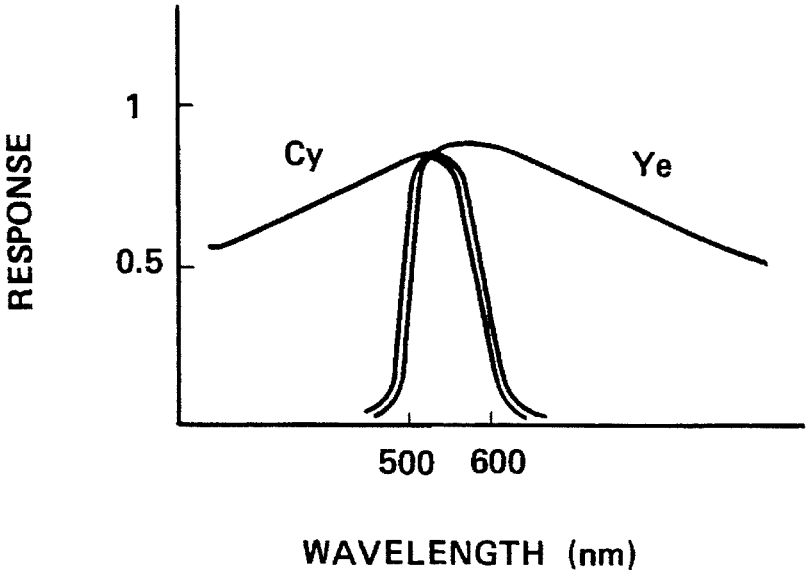

FIGS. 8 to 10 shows the third embodiment of the present invention.

This embodiment is applied to an electronic endoscope imaging apparatus in which a simultaneous system is adopted in the present invention.

In FIG. 8, an electronic endoscope imaging apparatus 40 is provided with a light source part [41] and a control part [42].

The light source part [41] is formed of a lamp 11 emitting illuminating light having wavelengths in the ultraviolet light range to the visible light range and further to the infrared light range, a lamp power source circuit 12 feeding an electric power to this lamp, a tone correcting filter 43 cutting the ultraviolet (UV) wavelength range and infrared (IR) wavelength range of the illuminating light emitted from the lamp 11 and a filter removably interposing means 34 removably interposing the above mentioned tone correcting filter 43 in the optical axis connecting the above mentioned lamp 11 with the light guide 4.

An observing optical system 5 and a solid state imaging device photoelectrically converting an observed image light are arranged on the tip side of an insertable part 3 of an endoscope 2. A color separating filter 44 separating the observed image light is secured on the front surface of the photoelectrically converting zone of this solid state imaging device and is provided mosaic-like with filters transmitting the respective color light of cyanine (Cy), green (G) and yellow (Ye).

Further, the above mentioned endoscope imaging apparatus 40 is formed of a CCD driving circuit 18 driving the above mentioned solid state imaging device 6, a pre-amplifying circuit 19 amplifying the electric signal including the picture image information output from the above mentioned solid state imaging device 6, a synchronous signal generating circuit 25 generating a reference signal of the entire endoscope imaging apparatus 40 and a control part [42] processing and subtracting video signals.

The above mentioned control part [42] is provided with an LPF 45 connected to the pre-amplifying circuit 19 and separating a luminance signal from the electric signal including the picture image information output from this preamplifying circuit 19. This LPF 45 is connected to a γ correcting circuit 46 correcting γ.

Also, the above mentioned pre-amplifying circuit 19 is connected to a BPF 47 separating the frequency of the color signal component. This BPF 47 is connected to a color separating circuit 50 formed of a 1H delay line 48, adding circuit 49a and subtracting circuit [496] *49b*. The adding circuit 49a forming this color separating circuit 50 is to add a 1H delay signal and an output signal of the BPF 47 and separate a blue signal. The subtracting circuit 49b is to subtract the 1H delay signal and the output signal of the BPF 47 and separate a red signal. The separated red and blue signals will be output respectively to a γ correcting circuit 51 correcting the color γ of the red (R) component and correcting circuit 52 correcting the color γ of the blue (B) component. The γ correcting circuit 51 is connected to a demodulating circuit 53 demodulating the red (R) component. The γ correcting circuit 52 is connected to a demodulating circuit 54 demodulating the blue (B) component.

Further, the above mentioned pre-amplifying circuit 19 is connected to an LPF 55 separating the green (G) component in the video signal. The output of this LPF 55 will be input into a γ correcting circuit 56 correcting γ of green (G).

The output signals of the above mentioned demodulating circuits 53 and 54 and γ correcting circuit 56 color-separated into the wavelength ranges of red (R), green (G) and blue (B) will be input into a subtracting circuit 24 subtracting the respective output signals. The color-separated output signals will be input into a color encoder circuit 57 and will be converted to color difference signals.

The video signal from the above mentioned subtracting circuit 24 and the color video signal in the general visible light range from the above mentioned color encoder circuit 57 will be input into a changing circuit 58, either of these signals will be selected and the selected video signal will be output to a television monitor 8.

The output signal of the γ correcting circuit 46 will be input into a level sensing circuit [41] *20* adjusting the exposure of the lamp 11.

The operation of the thus formed third embodiment shall be explained in the following.

The illuminating light emitted from the lamp 11 enters a light guide 4 on the end surface along an optical axis 15, is led through this light guide and is emitted from the exit end surface to illuminate a part to be observed (not illustrated). The observed image light from the observed part will be made to form an image on the color separating filter 44 by the observing optical system 5, will be separated into the colors of cyanine (Cy), green (G) and yellow (Ye), will be photoelectrically converted by the solid state imaging device 6, will be read out as electric signals including the picture image information by cyanine (Cy), green (G) and yellow (Ye) by the CCD driving circuit 18 synchronized with the reference signal of the synchronous signal generating circuit 25 and will be amplified by the pre-amplifying circuit 19.

In order to separate the luminance components and color components of the electric signals including the amplified picture image information, the electric signals in the frequency bands including the picture image information of the component in the red (R) wavelength range and the component in the blue (B) wavelength range are taken out by the BPF 47. The component in the red (R) wavelength range and the component in the blue (B) wavelength range are separated by the color separating circuit 50 and are γ corrected respectively by the γ correcting circuits 51 and 52, are demodulated respectively by the demodulating circuits 53 and 54 and are then input into the color encoder circuit 57.

On the other hand, the component in the green (G) wavelength range can be separated by taking out the output of the pre-amplifying circuit 19 by the LPF 55 and correcting γ by the γ correcting circuit 56.

Here, the same as is shown in the first and second embodiments, of the respective electric signals including the picture image information of the red (R), green (G) and blue (B) wavelength ranges different in the penetrating degrees in the mucous membrane surface layer of a living body, the red (R) component high in the penetrating degree and including the picture image information of the mucous membrane surface and below the mucous membrane and the blue (B) component low in the penetrating degree and including mostly the picture image information of the mucous membrane are subtracted to obtain a video signal sensing the picture image information below the mucous membrane.

The changing circuit 58 generates an NTSC signal by the color difference signal output from the color encoder circuit 57 and the luminance signal output from the γ correcting circuit 46 and changes it for the video signal, output from the subtracting circuit 24, to combine the subtraction optimum to the observed part and to compare it with an ordinary color picture image.

At this time, when obtaining the ordinary color picture image, in order to arrange the tone, a tone correcting filter 43 cutting the illuminating light in the infrared wavelength range and ultraviolet wavelength range is interposed in the optical axis 15 by a filter removably interposing means 34.

Now, FIG. 10 shows spectral output characteristics in the solid state imaging device 6 of cyanine (Cy), green (G) and yellow (Ye) using an array of color filters 44.

Thus, according to this embodiment, by using the simultaneous system, the same as in the first embodiment, by the difference in the penetrating degrees by the respective wavelength ranges in the observe part of the living body, not only the picture image information of the mucous membrane surface but also the penetrating range of the disease and the vein image below the mucous membrane can be observed at a high resolution without being influenced by the reflection on the mucous membrane surface.

The optical filters arranged in the rotary filter 16 and having transmitting characteristics in the specific wavelength ranges may be of a supplementary color system.

The subtraction may be made by an analogue signal instead of the digital signal.

With regard to the observed part in which the penetrating degrees of the illuminating light in the respective wavelength ranges will be influenced by colors other than hemoglobin, the wavelength ranges longer and shorter than the wavelength of 600 nm. as a boundary are not limited to be substracted but any combination may be used.

Further, in the respective embodiment, by changing the subtraction combination from a large penetrating degree wavelength range to a small penetrating degree wavelength range, the picture image information corresponding to the respective penetrating degrees can be obtained. For example, the penetrating range variations of the disease in the respective depths can be observed.

Figure 11:
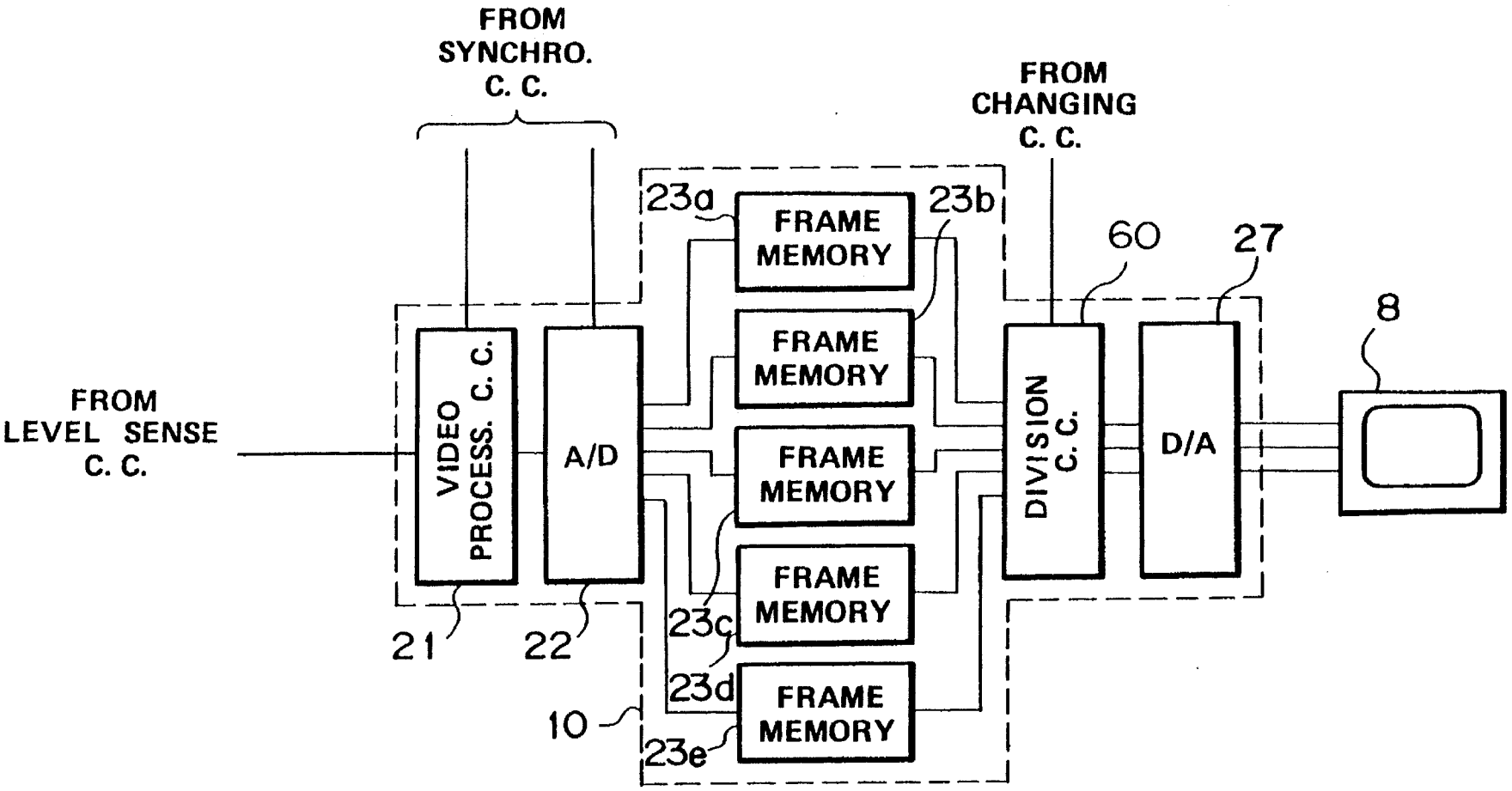
FIG. 11 relates to the fourth embodiment of the present invention and is an explanatory view showing the formation of an endoscope imaging apparatus having a dividing circuit.

FIG. 11 shows the fourth embodiment of the present invention.

In this embodiment, as a means of sensing the signal difference between picture image signals, a television circuit is provided instead of the subtracting circuit but the other formations are the same as in the first embodiment.

Frame memories 23a, 23b, 23c, 23d and 23e provided within the control part 10 are connected to a dividing circuit 60 which is controlled by a changing circuit 26 designating any video signals from among a plurality of video signals stored in the frame memories 23a, 23b, 23c, 23d and 23e. The video signals designated in this dividing circuit 60 will be divided.

The result of the operation in the above mentioned dividing circuit 60 will be analogized by the D/A converting circuit 27 and will be output on the television monitor 8.

The endoscope imaging apparatus in the present invention is not limited to the electronic endoscope but can be used also on an externally fitted camera to be used on a fiber scope and a TV camera for observing a living body.

As explained above, according to the present invention, by sensing a signal difference between at least two kinds of picture image signals obtained by using illuminating light by wavelengths different in the penetrating degrees, the reduction of the resolution by the reflected light on the mucous membrane surface, which has been the greatest problem, when observing, for example, the part below the mucous membrane within a living body cavity or the like can be prevented. Therefore, there is an effect that the vein running state and disease penetrating range below the mucous membrane in the observed part can be observed at a high resolution.

What is claimed is:

1. An endoscope apparatus comprising:

an elongated insertable part having an illuminating window and observing window in a tip part;

a light source part emitting an illuminating light;

a light guide means, inserted through said insertable part, for transmitting said illuminating light and for illuminating an object from said illuminating window;

an imaging means for receiving [the] reflected light from said object through said observing window and for converting said reflected light to an electric signal;

a light separating means interposed in an optical path of said illuminating light between said light source part and imaging means, for separating the light entering said imaging means into a plurality of wavelength bands, said light includes at least a range other than a visible range;

a video signal processing means for processing the [output] *electric* signal of said imaging means to produce a [video signal] *plurality of video signals*;

an operating means for removing video information included in one video signal by operating on at least two of a plurality of video signals based on light of said plurality of wavelength bands separated by said light separating means which are output signals of said video signal processing means;

a changing means for selecting at least one of the video image information output by said operating means and a video signal and for composing a usual color observing picture image output from said signal processing means; and a monitor means for displaying a picture image from input signals selected by said changing means.

2. An endoscope apparatus according to claim 1 wherein said operating means is a subtracting means detecting the signal difference between at least two video signals among the video signals corresponding to different wavelength bands.

3. An endoscope apparatus according to claim 1 wherein said operating means is a dividing means dividing at least two video signals among the video signals corresponding to different wavelength bands.

4. An endoscope apparatus according to claim 2 wherein said light separating means is formed of wavelength band transmitting filters transmitting respective wavelength bands of infrared rays, red, green, blue and ultraviolet rays and is interposed in time series in the optical path of the illuminating light between said light source part and light guide means.

5. An endoscope apparatus according to claim 2 wherein said light separating means is formed of wavelength band transmitting filters transmitting respective wavelength bands of red including infrared rays, green and blue including ultraviolet rays and is interposed in time series in the optical path of the illuminating light between said light source part and light guide means and an infrared ray removing filter not transmitting infrared rays and selectively interposed also in the optical path of the illuminating light between said light source part and light guide means.

6. An endoscope apparatus according to claim 2 wherein said light separating means comprises an infrared ray and ultraviolet ray removing filter not transmitting the wavelength bands of ultraviolet rays and infrared rays and selectively interposed in the optical path of the illuminating light between said light source part and light guide means and a color separating filter fixedly interposed between said object and imaging means and having transmitting parts transmitting the respective wavelength band of yellow including infrared rays, green and cyanine including ultraviolet rays arranged in the form of a mosaic.

7. An endoscope apparatus having as light separating means according to claim 4 or 5 wherein said subtracting means has a plurality of storing parts memorizing the video signals of the illuminating light having passed through the respective wavelength band transmitting filters and detects a signal difference of the video signals stored in said plurality of memorizing parts.

8. An endoscope apparatus having a light separating means according to claim 6 wherein said subtracting means detects a signal difference between two color signals output from a color separating part color-separating the electric signal from the imaging means.

9. An endoscope apparatus having a color separating means according to claim 4 wherein said subtracting means according to claim 4 wherein said subtracting means is controlled by said changing means to one of either making a subtraction to an input signal and outputting the input signal as is without being subtracted.

10. An endoscope apparatus having a light separating means according to claim 5 wherein said subtracting means is controlled by said changing means to one of either making a subtraction to an input signal and outputting an input signal as is without being subtracted.

11. An endoscope apparatus having a light separating means according to claim 6 wherein said changing means has input thereto a a) difference of a signal detected by said subtracting means and b) a video signal by a visible light produced from a color signal, and outputs either of c) the difference of the signal and d) the video signal by the visible light to said monitor means.

12. An endoscope apparatus according to claim 10 wherein said changing means will pull said infrared ray removing filter out from between said light source part and light guide means when detecting a signal difference and will interpose said infrared ray removing filter between said light source part and light guide means when subtraction is not made.

13. An endoscope apparatus according to claim 11 wherein said changing means will pull said infrared ray and ultraviolet ray removing filter out from between said light source part and light guide means when outputting a signal difference and will interpose said infrared ray and ultraviolet ray removing filter between said light source part and light guide means when outputting a video signal by a visible light.

14. An endoscope apparatus according to claim 3 wherein said light separating means is formed of a wavelength band transmitting filter transmitting respective wavelength bands of infrared, red, green, blue and ultraviolet rays and interposed in time series in the optical path of the illuminating light between the light source part and light guide means.

15. An endoscope apparatus having a light separating means according to claim 14 wherein said dividing means has a plurality of storing parts memorizing the video signals of the illuminating light having passed through the respective wavelength band transmitting filters and detects the signal difference between the video signals stored in the plurality of memorizing parts.

16. An endoscope apparatus having a light separating means according to claim 14, wherein said dividing means is controlled by said changing means to one of either dividing the input signal and outputting the input signal as is without being divided.

*17. An endoscope apparatus comprising:*

*an elongated insertable part having an illuminating window and observing window in a tip part;*

*a light source part emitting an illuminating light;*

*a light guide means, inserted through said insertable part, for transmitting said illuminating light and for illuminating an object from said illuminating window;*

*an imaging means for receiving reflected light from said object through said observing window and for converting said reflected light to an electric signal;*

*a light separating means interposed in an optical path of said illuminating light between said light source part and imaging means, for separating the light entering said imaging means into a plurality of wavelength bands;*

*a video signal processing means for processing the electric signal of said imaging means to produce a plurality of video signals;*

*an operating means for removing video information included in one video signal by operating on at least*

*two of a plurality of video signals based on light of said plurality of wavelength bands separated by said light separating means which are output signals of said video signal processing means;*

*a changing means for selecting at least one of the video image information output by said operating means and a video signal and for composing a usual color observing picture image output from said signal processing means; and*

*a monitor means for displaying a picture image from input signals selected by said changing means.*

*18. An endoscope apparatus according to claim 17 wherein said operating means is a subtracting means detecting the signal difference between at least two video signals among the video signals corresponding to different wavelength bands.*

*19. An endoscope apparatus according to claim 17 wherein said operating means is a dividing means dividing at least two video signals among the video signals corresponding to different wavelength bands.*

*20. An endoscope apparatus according to claim 18 wherein said light separating means is formed of wavelength band transmitting filters transmitting respective wavelength bands of infrared rays, red, green, blue and ultraviolet rays and is interposed in time series in the optical path of the illuminating light between said light source part and light guide means.*

*21. An endoscope apparatus according to claim 18 wherein said light separating means is formed of wavelength band transmitting filters transmitting respective wavelength bands of red including infrared rays, green and blue including ultraviolet rays and is interposed in time series in the optical path of the illuminating light between said light source part and light guide means and an infrared ray removing filter not transmitting infrared rays and selectively interposed also in the optical path of the illuminating light between said light source part and light guide means.*

*22. An endoscope apparatus according to claim 18 wherein said light separating means comprises an infrared ray and ultraviolet ray removing filter not transmitting the wavelength bands of ultraviolet rays and infrared rays and selectively interposed in the optical path of the illuminating light between said light source part and light guide means and a color separating filter fixedly interposed between said object and imaging means and having transmitting parts transmitting the respective wavelength bands of yellow including infrared rays, green and cyanine including ultraviolet rays arranged in the form of a mosaic.*

*23. An endoscope apparatus having a light separating means according to claim 20 and 21 wherein said subtracting means has a plurality of memorizing parts storing the video signals of the illuminating light having passed through the respective wavelength band transmitting filters and detects a signal difference of the video signals stored in said plurality of memorizing parts.*

*24. An endoscope apparatus having a light separating means according to claim 22 wherein said subtracting means detects a signal difference between two color signals output from a color separating part color-separating the electric signal from the imaging means.*

*25. An endoscope apparatus having a color separating means according to claim 20 wherein said subtracting means is controlled by said changing means to one of either making a subtraction to an input signal and outputting the input signal as is without being subtracted.*

*26. An endoscope apparatus having a light separating means according to claim 21 wherein said subtracting means is controlled by said changing means to one of either making a subtraction to an input signal and outputting an input signal as is without being subtracted.*

*27. An endoscope apparatus having a light separating means according to claim 22 wherein said changing means has input thereto a) a difference of a signal detected by said subtracting means and b) a video signal by a visible light produced from a color signal, and outputs either of c) the difference of the signal and d) the video signal by the visible light to said monitor means.*

*28. An endoscope apparatus according to claim 25 wherein said changing means will pull said infrared ray removing filter out from between said light source part and light guide means when detecting a signal difference and will interpose said infrared ray removing filter between said light source part and light guide means when subtracting is not made.*

*29. An endoscope apparatus according to claim 27 wherein said changing means will pull said infrared ray and ultraviolet ray removing filter out from between said light source part and light guide means when outputting a signal difference and will interpose said infrared ray and ultraviolet ray removing filter between said light source part and light guide means when outputting a video signal by a visible light.*

*30. An endoscope apparatus according to claim 19 wherein said light separating means is formed of a wavelength band transmitting filter transmitting respective wavelength bands of infrared, red, green, blue and ultraviolet rays and interposed in time series in the optical path of the illuminating light between the light source part and light guide means.*

*31. An endoscope apparatus having a light separating means according to claim 30 wherein said dividing means has a plurality of memorizing parts storing the video signals of the illuminating light having passed through the respective wavelength band transmitting filters and detects the signal difference between the video signals stored in the plurality of memorizing parts.*

*32. An endoscope apparatus having a light separating means according to claim 30 wherein said dividing means is controlled by said changing means to be one of either dividing the input signal and outputting the input signal as is without being divided.*

* * * * *